United States Patent [19]

Vandenberk et al.

[11] Patent Number: 4,665,075

[45] Date of Patent: May 12, 1987

[54] DERIVATIVES OF HYDROXY- OR AMINO-SUBSTITUTED (PIPERIDINYLALKYL)QUINAZOLINES

[75] Inventors: Jan Vandenberk, Beerse; Ludo E. J. Kennis; Josephus C. Mertens, both of Turnhout, all of Belgium

[73] Assignee: Janssen Pharmaceutica N.V., Beerse, Belgium

[21] Appl. No.: 780,147

[22] Filed: Sep. 26, 1985

Related U.S. Application Data

[63] Continuation-in-part of Ser. No. 678,422, Dec. 5, 1984, abandoned.

[51] Int. Cl.[4] ............... A61K 31/505; C07D 401/14; C07D 401/04

[52] U.S. Cl. .................... 514/259; 544/284; 544/285

[58] Field of Search ............... 544/285, 284; 514/259

[56] References Cited

U.S. PATENT DOCUMENTS 4,335,127 6/1982 Vandenberk et al. ............... 544/286

Primary Examiner—Glennon H. Hollrah
Assistant Examiner—James H. Turnispeed
Attorney, Agent, or Firm—Geoffrey G. Dellenbaugh

[57] ABSTRACT

Novel derivatives of hydroxy- or amino-substituted (piperidinylalkyl)quinazolines which are useful agents in the treatment of warmblooded animals suffering from diseases according to the vascular bed in which excessive serotonin release occurs.

18 Claims, No Drawings

DERIVATIVES OF HYDROXY- OR AMINO-SUBSTITUTED (PIPERIDINYLALKYL)QUINAZOLINES

REFERENCED TO RELATED APPLICATIONS

This is a continuation-in-part of our co-pending application Ser. No. 678,422 filed Dec. 5, 1984, now abandoned.

BACKGROUND OF THE INVENTION (Piperidinylalkyl)-quinazoline derivatives having potent serotonin-antagonistic properties have been described in U.S. Pat. No. 4,335,127. The compounds of the present invention differ from the hereinabove-mentioned prior-art compounds by their substitution on the quinazoline moiety and by their increased serotonin-antagonistic properties.

DESCRIPTION OF THE PREFERRED EMBODIMENTS

The present invention is concerned with quinazoline derivatives which are structurally represented by the formula and the pharmaceutically acceptable acid addition salts thereof, wherein R is hydrogen or $C_{1-6}$ alkyl;
$R^1$ is hydroxy, $C_{1-10}$ alkylcarbonyloxy, amino, mono- and di($C_{1-6}$ alkyl)amino, $C_{1-10}$ alkylcarbonylamino, phenylmethoxy or an azido group;
$R^2$ is hydrogen or halo;
$Y^1$ and $Y^2$ are each independently O or S;
Alk is a $C_{1-6}$ alkanediyl radical; and
Q is 1H-indol-3-yl or a radical of formula —X—Ar   (a)

wherein Ar is aryl; and X is a bivalent radical selected from the group consisting of, >C=O; >CHOH; >CH—O—C(=O)—$R_a$; >CH$_2$; >C(O—$C_{1-6}$ akyl)$_2$;

>C=NOH and >C=N—NH$_2$, said $R_a$ being hydrogen or $C_{1-6}$ alkyl and said q being the integer 2 or 3;
wherein aryl as used in the definition of Ar is phenyl optionally substituted with up to three halo-, $C_{1-6}$ alkyl-, $C_{1-6}$ alkyloxy-, trifluoromethyl or amino groups, thienyl or pyridinyl.

In the foregoing definitions the term halo is generic to fluoro, chloro, bromo and iodo; "$C_{1-6}$ alkyl" is meant to include straight and branched saturated hydrocarbon radicals, having from 1 to 6 carbon atoms, such as, for example, methyl, ethyl, 1-methylethyl, 1,1-dimethylethyl, propyl, butyl, pentyl, hexyl and the like; "$C_{1-10}$ alkyl" is meant to include $C_{1-6}$ alkyl radicals, as defined hereinabove, and the higher homologs thereof having from 7 to 10 carbon atoms; and "$C_1$–$C_6$ alkanediyl" is meant to include bivalent straight or branch chained alkanediyl radicals having from 1 to 6 carbon atoms.

Preferred compounds within the scope of formula (I) are those wherein $R^1$ is hydroxy, amino, acetylamino or azido, $R^2$ is hydrogen, R is hydrogen and Q is —CO—Ar.

Particularly preferred compounds within the scope of formula (I) are those wherein R, $R^1$ and $R^2$ are described for the preferred compounds, and wherein Q is —CO—Ar, wherein Ar is halophenyl.

Most preferred compounds within the scope of formula (I) are 3-[2-[4-(4-fluorobenzyl)-1-piperidinyl]ethyl]-6-hydroxy-2,4(1H,3H)-quinazolinedione, 7-amino-3-[4-(4-fluorobenzoyl)-1-piperidinyl]butyl-2,4(1H,3H)-quinazoline-dione, 7-azido-3-[2-[4-(4-fluorobenzoyl)-1-piperidinyl]ethyl]-2,4-(1,3H)-quinazolinedione and their pharmaceutically acceptable acid-addition salts.

The compounds of formula (I) can generally be prepared by reacting an appropriate reactive ester of formula (II) with a piperidine of formula (III).

In (II) and (III) $R^1$, $R^2$, $Y^1$, $Y^2$, Alk, R and Q are as previously defined and W is a reactive ester residue such as, for example, halo, e.g. chloro, bromo or iodo, or a sulfonyloxy radical such as methylsulfonyloxy, 4-methylphenylsulfonyloxy and the like.

The above-mentioned reactions are conveniently conducted in an inert organic solvent such as, for example, an aromatic hydrocarbon, e.g., benzene, methylbenzene, dimethylbenzene, and the like; a lower alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like, N,N-dimethylformamide (DMF); N,N-dimethylacetamide (DMA); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of an iodide salt, preferably an alkali metal iodide, is appropriate. Somewhat elevated temperatures may enhance the rate of the reaction.

In order to simplify the structural representation of the compounds of formula (I) and of certain intermediates thereof the radical of formula

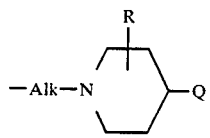

will hereinafter be represented by the symbol D.

The compounds of formula (I) may also be prepared by cyclizing an intermediate of formula (IV) with an amine of formula (V).

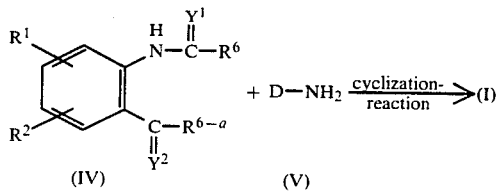

In (IV) $R^6$ and $R^{6-a}$ represent each an appropriate leaving group such as, for example, $C_{1-6}$ alkyloxy, amino and mono- and di($C_{1-6}$ alkyl)amino.

In the reaction of (IV) with (V) the intermediately formed amide of formula

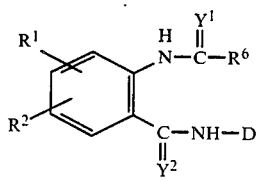

may be isolated before the start of the cyclization-reaction.

Additionally, the compounds of formula (I) may be prepared by cyclizing an isocyanate or isothiocyanate of formula (VII) with an amine of formula (V).

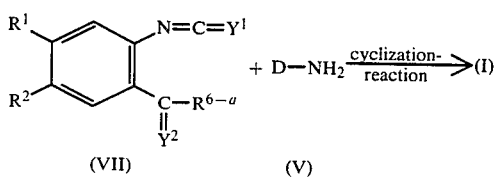

Said cyclization-reactions are conveniently conducted by heating the reactants together, optionally in a suitable reaction-inert solvent having a relatively high boiling point such as aliphatic and aromatic hydrocarbons, e.g. petroleumether, dimethylbenzene and the like, an ether, e.g. tetrahydrofuran, water and the like. The presence of a suitable base, e.g. an alkalimetal or earth alkaline metal hydroxide, such as potassium hydroxide and the like, may enhance the rate of the reaction.

The compounds of formula (I) wherein $R^1$ is amino, said compounds being represented by the formula (I-a), may also be derived from the corresponding nitro-substituted quinazolines of formula (VIII) following art-known nitro-to-amine reduction procedures.

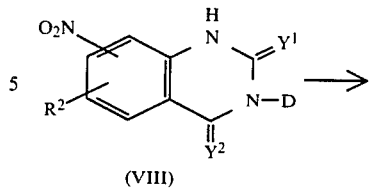

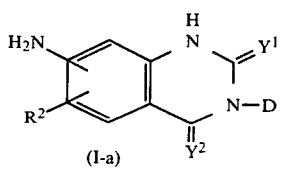

A suitable nitro-to-amine reducing procedure is, for example, catalytic hydrogenation in a relatively polar solvent such as, for example, an alcohol, e.g. methanol or ethanol, in the presence of an appropriate catalyst, e.g. platinum-on-charcoal. In some cases it may be useful to add an appropriate catalyst poison, e.g. thiophene.

The compounds of formula (I) may also be converted into each other following art-known functional group transformation procedures.

For example, the compounds of formula (I) wherein $R^1$ is phenylmethoxy may be converted into compounds of formula (I) wherein $R^1$ is hydroxy following art-known catalytic hydrogenolysis procedures; the compounds of formula (I) wherein $R^1$ is amino or hydroxy may be converted into compounds of formula (I) wherein $R^1$ is $C_{1-6}$ alkylcarbonylamino or $C_{1-6}$ alkylcarbonyloxy respectively by reacting the former compounds with a suitable acylating agent, e.g. an acylhalide or an acid anhydride; the compounds of formula (I) wherein $R^1$ is an amino-group may be converted into compounds of formula (I) wherein $R^1$ is an azido-group by converting the amino-group into a diazonium group with nitrous acid or an appropriate alkalimetal or earth alkaline metal thereof and subsequently converting the said diazonium group into an azide group with sodium azide or any other suitable alkalimetal or earth alkaline metal azide; the compounds of formula (I) wherein $R^2$ is hydrogen may be converted into compounds of formula (I) wherein $R^2$ is halo following art-known procedures for halogenating aromatic rings; compounds of formula (I) wherein Q is —CO—Ar may be converted into compounds of formula (I) wherein Q is —CHOH—Ar following art-known carbonyl-to-alcohol reducing procedures, e.g. by using sodiumborohydride as reductans; and compounds of formula (I) wherein X in X—Ar is >C—(O—$C_{1-6}$ alkyl)$_2$ or

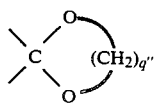

may be converted into compounds of formula (I) wherein Q is —CO—Ar by reacting the former with a suitable acid.

The intermediates and starting materials in the foregoing preparations may be prepared according to art-known methodologies for preparing said or similar chemical compounds, as described, for example in U.S. Pat. No. 4,335,127.

The compounds of formula (I) have basic properties and, consequently, they may be converted to their therapeutically active non-toxic acid addition salt forms by treatment with appropriate acids, such as, for example, inorganic acids, such as hydrohalic acid, e.g. hydrochloric, hydrobromic and the like, and sulfuric acid, nitric acid, phosphoric acid and the like; or organic acids, such as, for example, acetic, propanoic, hydroxyacetic, 2-hydroxy-propanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, benzoic, 2-hydroxybenzoic, 3-phenyl-2-propenoic, α-hydroxybenzeneacetic, 4-amino-2-hydroxybenzoic and the like acids. Conversely the salt form can be converted by treatment with alkali into the free base form.

The compounds of formula (I) and their pharmaceutically active acid addition salts have useful pharmacological properties. They are very potent serotonin-antagonists and as such they can be used in the treatment of a variety of diseases in which serotonin release is of predominant importance.

The potency of the subject compounds as serotonin-antagonistss is clearly evidenced by the results obtained in the following tests wherein the antagonistic activity of the compounds (I) on the effect of serotonin is examined.

Test 1: Antagonistic activity on the effect of serotonin on the caudal artery of the rat Caudal arteries from fasted male rats (210–235 g) were used in the test. Two helical strips having a length of 5–6 cm and a width of 2 mm were obtained from each artery and mounted vertically in a 100 ml organ bath containing an oxygenated Krebs-Henseleit solution. Submaximal contractions of the arterial strips were produced by adding single doses of serotonin (40 ng/ml) to the organ bath for 2 minutes with each time an interval of 10 minutes. The amplitude of the contraction is measured before and 5 minutes after adding the drug. After washing out, the agonist was added again three times in order to see whether the contraction is restored and normalized.

The first column of table 1 shows the $ED_{50}$-values in ng/ml for a number of compounds of formula (I) in the above test. In this connection the $ED_{50}$-values are the minimal concentrations of the concerned drugs which reduce the amplitude of the contraction to at least 50% of its normal value.

Test 2: Effects in gastric lesion tests a. Lesions induced by compound 48/80:

Compound 48/80 (a mixture of oligomers obtained by condensation of 4-methoxy-N-methylbenzenethanamine and formaldehyde) is a potent releaser of vasoactive amines from endogenous stores such as, for example, histamine and serotonin. Rats injected with compound 48/80 exhibit consistent changes of blood flow in different vascular beds: cyanosis of the ears and the extremities are prominent within five minutes after injection of the compound; the rats die from shock within 30 minutes. The shock, followed by dead, can be avoided if the rats are pretreated with a classical H1 antagonist. However the stimulatory effects on gastric secretion are not suppressed so that rats treated with compound 48/80 and protected from shock by an H1 antagonist may exhibit all signs of intensive gastric gland activity: gross autopsy shows distended stomachs with abnormal contents and rough bright red patches all over the mucosa, corresponding to areas of disintegrated glands. A number of known serotonin antagonists such as, for examples, methysergide, cyproheptadine, cinanserin, mianserin, pipamperone, spiperone, pizotifen and metergoline, prevent completely the cyanosis of ears and extremities as well as the lesions in the glandular area of the stomach and the abnormal gastric distension.

b. Method:

Male rats of a Wistar inbred strain, weighing 220–250 g, were starved overnight, water being available ad libitum. The test compounds were administered orally as a solution or as a suspension in aqueous medium. A control rat and a "blank" rat receive the test compound. One hour later 5-[4-(diphenylmethyl)-1-piperazinylmethyl]-1-methyl-1H-benzimidazole-2-methanol is adhministered subcutaneously to all rats at the dose of 2.5 mg/kg. Two hours after the oral administration of the test compound the compound 48/80 (freshly solved in water at a concentration of 0.25 mg/ml) was injected intravenously into all rats (dose: 1 mg/kg) except the "blank" rats. Five minutes after the injection the intensity of purple-blue coloration (cyanosis) of the extremities was scored as 0 (absent), + (moderate) or + + (intense). Four hours after the intravenous injection of compound 48/80 the rats were decapitated and the stomachs were removed. Subsequently the stomachs were inspected for distension and contents (blood, fluid, food) and thoroughly rinsed. The macroscopic lesions were scored from 0 to + + +, 0 corrsponding to complete absence of visible lesions and the highest score corresponding to reddish rough patches covering more than half the glandular area.

The second column of table 1 shows for a number of compounds of formula (I) the doses (in mg/kg body weight) at which the distance of the stomach as well as the lesions in the glandular area of the stomach are completely absent in 50% of the test rats ($ED_{50}$-values). The compounds listed in table 1 are not given for the purpose of limiting the invention thereto but only to exemplify the useful pharmacological activities of all the compounds within the scope of formula (I).

TABLE 1

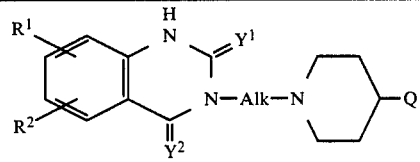

| No. | $R^1$ | $R^2$ | $Y^1$ | $Y^2$ | Alk | Q | Caudal artery ng/ml | Gastric lesion $ED_{50}$ in mg/kg |
|---|---|---|---|---|---|---|---|---|
| 8 | 7-$NH_2$ | H | O | O | $(CH_2)_4$ | 4-F—$C_6H_4$—CO— | 0.32 | 0.04 |

TABLE 1-continued

| No. | $R^1$ | $R^2$ | $Y^1$ | $Y^2$ | Alk | Q | Caudal artery ng/ml | Gastric lesion $ED_{50}$ in mg/kg |
|---|---|---|---|---|---|---|---|---|
| 9 | 7-$NH_2$ | H | S | O | $(CH_2)_2$ | 4-F—$C_6H_4$—CO— | 0.18 | 0.005 |
| 11 | 7-$NH_2$ | H | S | O | $(CH_2)_4$ | 4-F—$C_6H_4$—CO— | <0.63 | 0.63 |
| 12 | 7-$NH_2$ | H | O | O | $(CH_2)_2$ | 4-F—$C_6H_4$—CO— | <0.63 | 0.04 |
| 18 | 7-NHAc | H | O | O | $(CH_2)_4$ | 4-F—$C_6H_4$—CO— | 0.32 | 0.08 |
| 19 | 7-NHAc | H | S | O | $(CH_2)_2$ | 4-F—$C_6H_4$—CO— | 0.32 | 0.01 |
| 22 | 7-NHAc | H | O | O | $(CH_2)_2$ | 4-F—$C_6H_4$—CO— | 0.37 | 0.04 |

The compounds of formula (I) and their pharmaceutically acceptable acid addition salts are selective serotonin $S_2$-antagonists which bind with high affinity to $S_2$ (or 5-$HT_2$) receptors, directly antagonize serotonin-induced platelet activation and blood vessel contraction and prevent the functional consequences of serotonergic overstimulation such as vascular congestion and subsequent organ deficiency (e.g. gastric lesions). Consequently the compounds of the present invention can be used in the treatment of a broad spectrum of diseases according to the vascular bed in which excessive serotonin release occurs, primarily in hypertension and carcinoid syndrome but also in Raynaud's disease, gastrointestinal ulcus, scleroderma, hemorrhoids, irritable bowel syndrom and the like diseases whenever platelet activation with a thrombotic tendency or an excessive serotonin release from enterochromaffin cells is present.

In view of their useful selective serotonin $S_2$-antagonistic properties, the subject compounds may be formulated into various pharmaceuticaa forms for administration purposes. To prepare the pharmaceutical composition of this invention, an effective serotonin antagonistic amount of the particular compound, in base of acid-addition salt form, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions. It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

Although the amount of the active ingredient to be administered may vary within rather wide limits depending on the particular circumstances, such as the nature and the severity of the disease, doses of from about 0.04 to about 4 mg of active ingredient per kg of body weight, and particularly from about 0.1 to about 2 mg per kg of body weight, administered once or repeatedly, are in general satisfactory.

The following formulations exemplify typical serotonin antagonistic pharmaceutical compositions in dosage unit form suitable for systemic administration to animal and human subjects in accordance with the present invention. These examples are given to illustrate and not to limit the scope of the present invention.

"Active ingredient" (A.I.) as used throughout these formulations relates to a compound of formula (I) or a pharmaceutically acceptable acid-addition salt thereof.

ORAL DROPS

500 Grams of the A.I. was dissolved in 0.5 liters of 2-hydroxypropanoic acid and 1.5 liters of the polyethylene glycol at 60°–80° C. After cooling to 30°–40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

ORAL SOLUTION

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grms of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

CAPSULES

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

FILM-COATED TABLETS

Preparation of tablet core: A mixture of 100 grams of the A.I., 570 grams lactose and 200 grams starch was mixed well and thereafter humidified with a solution of 5 grams sodium dodecyl sulfate and 10 grams polyvinylpyrrolidone in about 200 milliliters of water. The wet powder mixture was sieved, dried and sieved again. Then there was added 100 grams microcrystalline cellulose and 15 grams hydrogenated vegetable oil. The whole was mixed well and compressed into tablets, giving 10.000 tablets, each containing 10 milligrams of the active ingredient.

Coating: To a solution of 10 grams methyl cellulose in 75 milliliters of denaturated ethanol there was added a solution of 5 grams of ethyl cellulose in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109) and the whole was homogenated.

The tablet cores were coated with the thus obtained mixture in a coating apparatus.

INJECTABLE SOLUTIONS 1.8 Grams methyl 4-hydroxybenzoate and 0.2 grams propyl 4-hydroxy-benzoate were dissolved in about 0.5 liters of boiling water for injection. After cooling to about 50° C. there were added while stirring 4 grams lactic acid, 0.05 propylene glycol and 4 grams of the A.I. The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

SUPPOSITORIES

3 Grams A.I. was dissolved in a solution of 3 grams 2,3-dihydroxy-butanedioic acid in 25 milliliters polyethylene glycol 400. 12 Grams surfactant and triglycerides q.s. ad 300 grams were molten together. The latter mixture was mixed well with the former solution. The thus obtained mixture was poured onto moulds at a temperature of 37°-38° C. to form 100 suppositories each containing 30 milligrams of the active ingredient.

In view of the serotonin antagonistic activity of the subject compounds, it is evident that the present invention provides a method of treating diseases of warm-blooded animals according to the vascular bed in which excessive serotonin release occurs by the systemic administration of an effective serotonin antagonistic amount of a compound of formula (I) or a pharmaceutically acceptable acid addition salt thereof in admixture with a pharmaceutical carrier.

The following examples are intended to illustrate and not to limit the scope of the present invention. Unless otherwise stated all parts therein are by weight.

EXPERIMENTAL PART

A. Preparation of intermediates

EXAMPLE 1

A mixture of 74.7 parts of 1-acetyl-4-[(4-fluorophenyl)carbonyl]piperidine, 46.5 parts of 1,2-ethanediol, 3 parts of 4-methylbenzenesulfonic acid and 810 parts of benzene was stirred and refluxed for 108 hours with water-separator. The reaction mixture was cooled and washed successively with a mixture of 250 parts of water and 22.5 parts of ammonium hydroxide, and with 250 parts of water. The organic phase was separated, dried, filtered and evaporated. The residue was purified by column chromatography over silica gel using a mixture of trichloromethane and 2-propanone (50:50 by volume) as eluent. The pure fractions were collected and the eluent was evaporated, yielding 50 parts (56.8%) of 1-acetyl-4-[(2-(4-fluorophenyl)-1,3-dioxolan-2-yl]piperidine as a residue (interm. 1).

A mixture of 5 parts of 1-acetyl-4-[2-(4-fluorophenyl)-1,3-dioxolan-2-yl]piperidine and 100 parts of a sodium hydroxide solution 10% was stirred and refluxed overnight. The reaction mixture was cooled and the product was extracted with trichloromethane. The extract was dried, filtered and evaporated. The solid residue was stirred in 2,2'-oxybispropane. The product was filtered off and dried in vacuo at 40° C., yielding 3.5 parts (82%) of 4-[2-(4-fluorophenyl)-1,3-dioxolan-2-yl]piperidine (2).

EXAMPLE 2

To a stirred and refluxed mixture of 25 parts of ethyl 4-hydroxy-2-nitrobenzoate, 11 parts of potassium carbonate and 200 parts of 2-propanone were added dropwise 21 parts of (bromomethyl)benzene. Upon completion, stirring was continued overnight at reflux temperature. After cooling, the whole was filtered and the filtrate was evaporated, yielding 25 parts (69%) of ethyl 2-nitro-4-(phenylmethoxy)benzoate as a residue (3).

A mixture of 25 parts of ethyl 2-nitro-4-(phenylmethoxy)benzoate and 160 parts of ethanol was hydrogenated at normal pressure and at room temperature with 5 parts of Raney-nickel catalyst. After the calculated amount of hydrogen was taken up, the catalyst was filtered off and the filtrate was evaporated. The residue was purified by column chromatography over silica gel using a mixture of trichloromethane and methanol (95.5 by volume) as eluent. The pure fractions were collected and the eluent was evaporated. The residue was boiled in 2,2'-oxybispropane. After cooling, the product was filtered off and dried, yielding 14.5 parts (65%) of ethyl 2-amino-4-(phenylmethoxy)benzoate (4).

EXAMPLE 3

A mixture of 5 parts of 4-chlorobutanenitrile, 10 parts of (4-fluorophenyl)(4-piperidinyl)methanone, 10 parts of sodium carbonate and 200 parts of 4-methyl-2-pentanone was stirred and refluxed overnight. The reaction mixture was filtered and the filtrate was evaporated. The oily residue was crystallized from 2,2'-oxybispropane. The product was filtered off and recrystallized from 2,2'-oxybispropane, yielding 6.1 parts of 4-(4-fluorobenzoyl)-1-piperidinebutanenitrile; mp. 100° C. (5).

Following the same procedure and using equivalent amounts of the appropriate starting materials there were also prepared:
4-(4-fluorobenzoyl)-1-piperidineacetonitrile (6);
4-(1H-indol-3-yl)-1-piperidineacetonitrile (7);
4-[2-(4-fluorophenyl)-1,3-dioxolan-2-yl]-1-piperidineacetonitrile (8); and
4-[2-(4-fluorophenyl)-1,3-dioxolan-2-yl]-1-piperidinebutanenitrile (9).

EXAMPLE 4

A mixture of 28 parts of 4-[2-(4-fluorophenyl)-1,3-dioxolan-2-yl]-1-piperidinebutanenitrile and 200 parts of methanol saturated with ammonia was hydrogenated at normal pressure and at room temperature with 5 parts of Raney nickel catalyst. After the calculated amount of hydrogen was taken up, the catalyst was filtered off over Hyflo and the filtrate was evaporated, yielding 25 parts (95%) of 4-[2-(4-fluorophenyl)-1,3-dioxolan-2-yl]-1-piperidinebutanamide as a residue (10).

In a similar manner there were also prepared:
[1-(2-aminoethyl)-4-piperidinyl](4-fluorophenyl)methanone as a residue; (11)
4-(1H-indol-3-yl)-1-piperidineethanamine; (12)
[1-(4-aminobutyl)-4-piperidinyl](4-fluorophenyl)methanone as a residue (13); and
4-[2-(4-fluorophenyl)-1,3-dioxolan-2-yl]-1-piperidineethanamine as a residue (14).

EXAMPLE 5

To a stirred mixture of 7 parts of ethyl 2-amino-4-(phenylmethoxy)benzoate and 45 parts of dimethylbenzene were added dropwise 3.25 parts of ethyl carbonochloridate. Upon completion, stirring was continued for 6 hours at reflux temperature. The reaction mixture was cooled and the solvent was evaporated. The residue was crystallized from 2,2'-oxybispropane. The product was filtered off and dried, yielding 6.1 parts (71%) of ethyl 2-[(ethoxycarbonyl)-amino]-4-(phenylmethoxy)-benzoate (15).

Following the same procedure and using equivalent amounts of the appropriate starting materials there were also prepared:
ethyl 2-(ethoxycarbonylamino)-5-hydroxybenzoate; mp. 119.7° C. (16); and
2-[(ethoxycarbonyl)amino]-5-(phenylmethoxy)benzoic acid (17).

EXAMPLE 6

To a stirred mixture of 5 parts of calcium carbonate, 18.75 parts of trichloromethane and 12.5 parts of water were added 3.6 parts of ethyl 2-amino-5-hydroxybenzoate. 3 Parts of concentrate hydrochloric acid and 10 parts of water were added and the whole was stirred for 15 minutes under nitrogen atmosphere. After cooling in an ice bath at 10° C., 2.6 parts of carbonothioic dichloride were added dropwise, during a period of 20 minutes, at 10°-15° C. The whole was allowed to reach room temperature and stirring was continued for 2 hours. 300 Parts of trichloromethane and 200 parts of water were added. The organic layer was separated, washed with a hydrochloric acid solution 1N and with a sodium hydrogen carbonate solution 10%, dried, filtered and evaporated. The residue was crystallized from 45 parts of benzene. The product was filtered off and dried, yielding 3.0 parts (67.1%) of ethyl 5-hydroxy-2-isothiocyanatobenzoate (18).

In a similar manner there were also prepared:
ethyl 2-isothiocyanato-4-(phenylmethoxy)benzoate as a residue (19).

EXAMPLE 7

To a stirred solution of 28 parts of [1-(4-aminobutyl)-4-piperidinyl](4-fluorophenyl)methanone in 135 parts of tetrahydrofuran was added dropwise during a 10 minutes-period a solution of 24 parts of methyl 2-isothiocyanato-4-nitrobenzoate in 180 parts of tetrahydrofuran (slightly exothermic reaction). Upon completion, stirring was continued overnight at room temperature. The solid was filtered off and crystallized from ethanol while stirring and cooling to 40° C. The product was filtered off, washed with ethanol and dried in vacuo at 80° C., yielding 30 parts (62%) of 3-[4-[4-(4-fluorobenzoyl)-1-piperidinyl]butyl]-2,3-dihydro-7-nitro-2-thioxo-4(1$\underline{H}$)-quinazolinone; mp. 225° C. (20).

Following the same procedure and using equivalent amounts of the appropriate starting materials there were also prepared:
3-[2-[4-(4-fluorobenzoyl)-1-piperidinyl]ethyl]-2,3-dihydro-7-nitro-2-thioxo-4(1$\underline{H}$)-quinazolinone (21); and
3-[2-[4-[2-(4-fluorophenyl)-1,3-dioxolan-2-yl]-1-piperidinyl]ethyl]-2,3-dihydro-7-nitro-2-thioxo-4(1$\underline{H}$)-quinazolinone; mp. 217.8° C. (22).

EXAMPLE 8

To a stirred mixture of 7 parts of 3-[2-[4-(4-fluorobenzoyl)-1-piperidinyl]ethyl]-2,3-dihydro-7-nitro-2-thioxo-4(1$\underline{H}$)-quinazolinone, 120 parts of a solution of potassium hydroxide in ethanol 5% and 10 parts of water were added dropwise 100 parts of a hydrogen peroxide solution 3% during a 10 minutes period. Upon completion, stirring was continued for 2.50 hours at room temperature. Then there were added 100 parts of water and the whole was neutralized with acetic acid. The precipitated product was filtered off and crystallized from a mixture of N,N-dimethylacetamide and water, yielding 4.8 parts of 3-[2-[4-(4-fluorobenzoyl)-1-piperidinyl]ethyl]-7-nitro-2,4(1$\underline{H}$,3$\underline{H}$)-quinazolinedione; mp. 238.1°-240.1° C. (23).

EXAMPLE 9

To a stirred mixture of 36 parts of 3-[4-[4-(4-fluorobenzoyl)-1-piperidinyl]butyl]-2,3-dihydro-7-nitro-2-thioxo-4(1$\underline{H}$)-quinazolinone, 700 parts of a potassium hydroxide solution in ethanol 5% and 150 parts of water were added 500 parts of a hydrogen peroxide solution 3% at room temperature. The whole was stirred overnight at room temperature. The mixture was neutralized with acetic acid. The product was filtered off, washed with water and 2-propanol and stirred in 2,2'-oxybispropane and thrichloromethane. The product was filtered off and dried, yielding 31 parts (88%) of 3-[4-[4-(4-fluorobenzoyl)-1-piperidinyl]butyl]-7-nitro-2,4(1$\underline{H}$,3$\underline{H}$)-quinazolinedione; mp. 188° C. (24).

EXAMPLE 10

To a stirred suspension of 19.6 parts of 2-[(ethoxycarbonyl)amino]-5-(phenylmethoxy)benzoic acid in 520 parts of dichloromethane were added 12.6 parts of N,N-diethylethanamine and the whole was stirred for 5 minutes. 15.9 Parts of 2-chloro-1-methylpyridinium iodide were added and stirring was continued for 90 minutes. A solution of 18.2 parts of 4-[2-(4-fluorophenyl)-1,3-dioxolan-2-yl]-1-piperidineethanamine in 390 parts of dichloromethane was added dropwise to the whole. Upon completion, stirring was continued for 2.50 hours at room temperature. 150 Parts of water were added to the reaction mixture. The organic layer was separated, washed with a sodium hydrogen carbonate solution 10%, dried, filtered and evaporated. The oily residue was purified by HPLC over silica gel using a mixture of methylbenzene and methanol (95:5 by volume) as eluent. The pure fractions were collected and the eluent was evaporated, yielding 24.7 parts (67%) of ethyl [2-[[[2-[4[2-(4-fluorophenyl)-1,3-dioxolan-2-yl]-1-piperidinyl]ethyl]aminocarbonyl]-4-(phenylmethoxy)phenyl]carbamate as a residue (25).

Following the same procedure and using equivalent amounts of the appropriate starting materials there were also prepared:
ethyl [2[[[2-[4-(4-fluorobenzoyl)-1-piperidinyl]ethyl]amino]carbonyl]4-(phenylmethoxy)phenyl]carbamate as a residue (26).

EXAMPLE 11

To a stirred mixture of 22.5 parts of 3-(2-chloroethyl)-2,4(1H3H)-quinazolinedione and 368 parts of sulfuric acid (d=1.84) were dded dropwise 8.1 parts of nitric acid (d=1.5) while the temperature was kept at room temperature by cooling in an ice-water bath. Upon completion, stirring at room temperature was continued for 3 hours. The reaction mixture was poured onto crushed ice. The precipitated product was washed three times with water and crystallized from methanol. Upon cooling, the product was filtered off and dried, yielding 25 parts (100%) of 3-(2-chloroethyl)-6-nitro-2,4(1H,3H)-quinazolinedione; mp. 251.2° C. (27).

EXAMPLE 12

A mixture of 16.2 parts of 3-(2-chloroethyl)-6-nitro-2,4(1H,3H)-quinazolinedione, 15 parts of 4-[2-(4-fluorophenyl)-1,3-dioxolan-2-yl]piperidine, 10 parts of sodium hydrogen carbonate, 0.1 parts of potassium iodide and 135 parts of N,N-dimethylformamide was stirred and heated overnight at 100°-120° C. The reaction mixture was cooled and poured onto water. Stirring was continued till complete precipitation. The precipitate was filtered off and dissolved in trichloromethane. The thus formed emulsion was dried, filtered and evaporated. The residue was crystallized from acetonitrile, yielding 18.6 parts (64%) of 3-[2-[4-[2-(4-fluorophenyl)-1,3-dioxolan-2-yl]-1-piperidinyl]ethyl]-6-nitro-2,4(1H,3H)-quinazolinedione; mp. 250.9° C. (28).

Following the same procedure and using equivalent amounts of the appropriate starting materials there were also prepared:
3-[2-[4-(4-fluorobenzoyl)-1-piperidinyl]ethyl]-6-nitro-2,4(1H,3H)-quinazolinedione (Z)-2-butenedioate(1:1).hemihydrate; mp. 213.7° C. (29); and
3-[2-[4-(1H-indol-3-yl)-1-piperidinyl]ethyl]-6-nitro-2,4(1H,3H)-quinazolinedione; mp. 228.2° C. (30).

B. Preparation of final compounds

EXAMPLE 13

A mixture of 12.5 parts of ethyl 2-(ethoxycarbonylamino)-5-hydroxybenzoate and 12 parts of 4-(1H-indol-3-yl)-1-piperidineethanamine was stirred in an oil bath at about 200° C. and under nitrogen atmosphere. The formed ethanol was distilled off. The whole was cooled and the solid product was crystallized from a mixture of ethanol and acetonitrile. The product was filtered off and dried, yielding 14.5 parts (70%) of 6-hydroxy-3-[2-[4-(1H-indol-3-yl)-1-piperidinyl]ethyl]-2,4(1H,3H)-quinazolinedione; mp. 258.2° C. (compound 1).

Following the same procedure and using equivalent amounts of the appropriate starting materials there were also prepared:
3-[2-[4-(4-fluorobenzoyl)-1-piperdinyl]ethyl]-6-hydroxy-2,4(1H,3H)-quinazolinedione monohydrochloride.monohydrate; mp. 275.7° C. (2); and
3-[4-[4-[2-(4-fluorophenyl)-1,3-dioxolan-2-yl]-1)-piperidinyl]butyl]-7-(phenylmethoxy)-2,4(1H,3H-quinazolinedione; mp. 215.2° C. (3).

EXAMPLE 14

A mixture of 9.3 parts of ethyl [2-[[[2-[4-(4-fluorobenzoyl)-1-piperidinyl]ethyl]amino]carbonyl]-4-(phenylmethoxy)phenyl]carbamate and 100 parts of a potassium hydroxide solution 10% in water was stirred in an oil-bath for 8 hours at 100° C. After cooling to room temperature, the precipitated product was filtered off, dried and boiled in 16 parts of methanol. Upon cooling to room temperature, the precipitated product was filtered off and dried in vacuo at 50° C., yielding 7.05 parts (83%) of 3-[2-[4-(4-fluorobenzoyl)-1-piperidinyl]ethyl]-6-(phenylmethoxy)-2,4-(1H,3H)-quinazolinedione (4).

In a similar manner there was also prepared:
3-[2-[4-[2-(4-fluorophenyl)-1,3-dioxolan-2-yl]-1-piperidinyl]-ethyl]-6-(phenylmethoxy)-2,4(1H,3H)-quinazolinedione (5).

EXAMPLE 15

To a stirred mixture of 6.25 parts of [1-(2-aminoethyl)-4-piperidinyl](4-fluorophenyl)methanone and 135 parts of tetrahydrofuran was added dropwise a solution of 7.5 parts of ethyl 2-isothiocyanato-4-(phenylmethoxy)benzoate in 45 parts of tetrahydrofuran. Upon completion, stirring was continued for 4 hours at room temperature and for 30 minutes at reflux temperature. After cooling, the product was filtered off and crystallized from a mixture of N,N-dimethylformamide and water. The product was filtered off and dried, yielding 3.8 parts (29%) of 3-[2-[4-(4-fluorobenzoyl)-1-piperidinyl]ethyl]-2,3-dihydro-7-(phenylmethoxy)-2-thioxo-4(1H)-quinazolinone; 236.0° C. (dec.) (6).

Following the same procedure and using equivalent amounts of the appropriate starting materials there was also prepared:
3-[2-[4-(4-fluorobenzoyl)-1-piperidinyl]ethyl]-2,3-dihydro-6-hydroxy-2-thioxo-4(1H)-quinazolinone monohydrochloride.monohydrate (7).

EXAMPLE 16

A mixture of 30 parts of 3-[4-[4-(4-fluorobenzoyl)-1-piperidinyl]-butyl]-7-nitro-2,4(1H,3H)-quinazolinedione, 500 parts of acetic acid and 2 parts of a solution of thiophene in methanol 4% was hydrogenated at normal pressure and at room temperature with 5 parts of palladium-on-charcoal catalyst 10%. After the calculated amount of hydrogen was taken up, the catalyst was filtered off over diatomaceous earth and the filtrate was evaporated. The residue was stirred in 80 parts of 2-propanol, 300 parts of water and 100 parts of ammonium hydroxide. The aqueous phase was decanted and the residue was crystallized from acetonitrile. The product was filtered off and dried, yielding 27 parts (96%) of 7-amino-3-[4-[4-(4-fluorobenzoyl)-1-piperidinyl]butyl]-2,4(1H,3H)-quinazolinedione; mp. 213.0° C. (8).

In a similar manner there were also prepared:
7-amino-3-[2-[4-(4-fluorobenzoyl)-1-piperidinyl]ethyl]-2,3-dihydro-2-thioxo-4(1H)-quinazolinone; mp. 262.6° C. (9);
7-amino-3-[2-[4-[2-(4-fluorophenyl)-1,3-dioxolan-2-yl]-1-piperidinyl]ethyl]-2,3-dihydro-2-thioxo-4(1H)-quinazolinone acetate(1:1) as a residue (10);
7-amino-3-[4-[4-(4-fluorobenzoyl)-1-piperidinyl]butyl]-2,3-dihydro-2-thioxo-4(1H)-quinazolinone; mp. 194.8° C. (11);
7-amino-3-[2-[4-(4-fluorobenzoyl)-1-piperidinyl]ethyl]-2,4(1H,3H)-quinazolinedione; mp. 266.3° C. (12);
6-amino-3-[2-[4-(4-fluorobenzoyl)-1-piperidinyl]ethyl]-2,4(1H,3H)-quinazolinedione; mp. 258.6° C. (13); and
6-amino-3-[2-[4-(1H-indol-3-yl)-1-piperidinyl]ethyl]-2,4(1H,3H)-quinazolinedione; mp. 277.0° C. (14).

EXAMPLE 17

A mixture of 1.2 parts of 3-[2-[4-(4-fluorobenzoyl)-1-piperidinyl]ethyl]-6-nitro-2,4(1H,3H)-quinazolinedione, 0.5 parts of a solution of thiophene in methanol 4% and 100 parts of acetic acid was hydrogenated at normal pressure and at room temperature with 1 part of platinum-on-charcoal catalyst 5%. After the calculated amount of hydrogen was taken up, the catalyst was filtered off and 10 parts of acetic acid anhydride were added to the filtrate. The whole was stirred and refluxed for 3 hours. After evaporation, water was added to the residue and the whole was treated with ammonia. The precipitated product was filtered off and converted into the (Z)-2-butenedioate salt in ethanol. From the latter the salt was crystallized at −5° C. The product was filtered off and dried, yielding 0.4 parts (32%) of N-[3-[2-[4-(4-fluorobenzoyl)-1-piperidinyl]ethyl]-1,2,3,4-tetrahydro-2,4-dioxo-6-quinazolinyl]-acetamide (Z)-2-butenedioate(1:1).monohydrate; mp. 170.7° C. (15).

EXAMPLE 18

A mixture of 19.25 parts of 3-[2-[4-[2-(4-fluorophenyl)-1,3-dioxolan-2-yl]-1-piperidinyl]ethyl]-6-(phenylmethoxy)-2,4(1H,3H)-quinazolinedione and 525 parts of 2-methoxyethanol was hydrogenated at normal pressure and at room temperature with 7 parts of palladium-on-charcoal catalyst 10%. After the calculated amount of hydrogen was taken up, the catalyst was filtered off and the filtrate was evaporated. The residue was stirred in boiling methanol. After cooling, the product was filtered off, yielding a first crude fraction of 8.6 parts. The filtrate was evaporated, yielding a second crude fraction of 7.1 parts. The combined crude fractions (respectively 8.6 parts and 7.1 parts) were stirred in boiling methanol. The precipitated product was filtered off at room temperature, washed with methanol and dried, yielding 13.8 parts of 3-[2-[4-[2-(4-fluorophenyl)-1,3-dioxolan-2-yl]-1-piperidinyl]-ethyl]-6-hydroxy-2,4(1H,3H)-quinazolinedione; mp. 245.8° C. (16). In a similar manner that was also prepared:
3-[4-[4-[2-(4-fluorophenyl)-1,3-dioxolan-2-yl]-1-piperidinyl]-butyl]-7-hydroxy-2,4(1H,3H)-quinazolinedione (17).

EXAMPLE 19

A mixture of 5.8 parts of 7-amino-3-[4-[4-(4-fluorobenzoyl)-1-piperidinyl]butyl]-2,4(1H,3H)-quinazolinedione, 100 parts of acetic acid and 2.5 parts of acetic acid anhydride was stirred at reflux temperature. The reaction mixture was evaporated. The residue was stirred in water and ammonium hydroxide. The product was filtered off, washed with water and boiled in ethanol. After cooling, the product was filtered off, washed with 2,2'-oxybispropane and dried, yielding 6.3 parts (100%) of N-[3-[4-[4-(4-fluorobenzoyl)-1-piperidinyl]butyl]-1,2,3,4-tetrahydro-2,4-dioxo-7-quinazolinyl]-acetamide; mp. 273.1° C. (18).

In a similar manner there were also prepared:
N-[3-[2-[4-(4-fluorobenzoyl)-1-piperidinyl]ethyl]-1,2,3,4-tetrahydro-4-oxo-2-thioxo-7-quinazolinyl]acetamide; mp. 246.9° C. (19);
N-[3-[2-4-[2-(4-fluorophenyl)-1,3-dioxolan-2-yl]-1-piperidinyl]-ethyl]-1,2,3,4-tetrahydro-4-oxo-2-thioxo-7-quinazolinyl]acetamide monohydrate; mp. 240.7° C. (20).
N-[3-[4-[4-(4-fluorobenzoyl)-1-piperidinyl]butyl]-1,2,3,4-tetrahydro-4-oxo-2-thioxo-7-quinazolinyl]acetamide; mp. 246.8° C. (21); and
N-[3-[2-[4-(4-fluorobenzyl)-1-piperidinyl]ethyl]-1,2,3,4-tetrahydro-2,4-dioxo-7-quinazolinyl]-acetamide; mp. 284.4° C. (22).

EXAMPLE 20

A mixture of 4.11 parts of 3-[2-[4-(4-fluorobenzoyl)-1-piperidinyl]ethyl]-6-hydroxy-2,4(1H,3H)-quinazolinedione and 10 parts of decanoic acid anhydride with ethyl hydrogen carbonate was stirred for 3 hours at 120° C. Stirring was continued overnight at 100° C. After cooling, water was added and the whole was treated with ammonia. The product was extracted with dichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from 2-propanol. The product was filtered off and dried, yielding 2.8 parts (90%) of 3-[2-[4-(4-fluorobenzoyl)-1-piperidinyl]ethyl]-1,2,3,4-tetrahydro-2,4-dioxo-6-quinazolinyl decanoate; mp. 169.0° C. (23).

In a similar manner there was also prepared:
3-[2-[4-(4-fluorobenzoyl)-1-piperidinyl]ethyl]-1,2,3,4-tetrahydro-2,4-dioxo-6-quinazolinol acetate(ester); mp. 228.8° C. (24).

EXAMPLE 21

To a stirred solution of 2.3 parts of 3-[2-[4-(4-fluorobenzoyl)-1-piperidinyl]ethyl]-2,3-dihydro-6-hydroxy-2-thioxo-4(1H)-quinazolinone monohydrochloride in 40 parts of methanol was added a sodium hydroxide solution 1N till pH=7. 0.37 Parts of sodium borohydride were added portionwise. Upon completion, stirring was continued for 20 hours at room temperature. The reaction mixture was poured into water. The whole was acidified with formic acid till pH=2. After stirring for 30 minutes at room temperature, the mixture was treated with ammonium hydroxide (an oily precipitate was formed). Trichloromethane was added. After 1 hour, the only precipitate was dissolved. The organic layer was separated and washed with water whereupon a precipitate was formed (=precipitate I). Then the organic layer was washed again with water, dried, filtered and evaporated (=residue I). Precipitate I and residue I were purified by column chromatography over silica gel using first a mixture of trichloromethane and methanol (90:10 by volume) and then a mixture of trichloromethane and methanol (80:20 by volume) as eluent. The second fraction was collected and the eluent was evaporated. The residue was boiled in 20 parts of 2-propanone and 17.5 parts of 2,2'-oxybispropane. The product was filtered off and dried at 100° C., yielding 0.6 parts (28.5%) of 3-[2-[4-[(4-fluorophenyl)hydroxymethyl]-1-piperidinyl]ethyl]-2,3-dihydro-6-hydroxy-2-thioxo-4(1H)-quinazolinone; mp. 218.0° C. (25). Following the same procedure and using equivalent amount of the appropriate starting materials there was also prepared:
3-[2-[4-[(4-fluorophenyl)hydroxymethyl]-1-piperidinyl]ethyl]-6-hydroxy-2,4(1H,3H)-quinazolinedione; mp. 150.1° C. (26).

EXAMPLE 22

A mixture of 1.9 parts of 3-[4-[4-[2-(4-fluorophenyl)-1,3-dioxolan-2-yl]-1-piperidinyl]butyl]-7-hydroxy-2,4(1H,3H)-quinazolinedione, 10 parts of a hydrochloric acid solution 6N and 20 parts of ethanol was stirred for 4 hours at reflux temperature. The base was liberated with ammonia. The product was filtered off and purified by column chromatography over silica gel using a mixture of trichloromethane and methanol (90:10 by volume) as eluent. The pure fractions were collected and the eluent was evaporated, yielding 0.5 parts (28%) of 3-[4-[4-(4-fluorobenzyl)-1-piperidinyl]butyl]-7-hydroxy-2,4(1H,3H)-quinazolinedione; mp. 207.9° C. (27).

EXAMPLE 23

To a stirred and cooled (5° C.) solution of 0.205 parts of 7-amino-3-[2-[4-(4-fluorobenzoyl)-1-piperidinyl]ethyl]-2,4(1H,3H)-quinazolinedione in 50 parts of an acetic acid solution 1N was added a solution of 0.1725 parts of sodium nitrite in 2 parts of water. The whole was stirred for 20 minutes at 5° C. A solution of 0.1625 parts of sodium azide in 2 parts of water was added and stirring was continued for 20 minutes at 5° C. in vacuo. 5.5 Parts of a sodium hydroxide solution 10N were added whereupon the product solidified. The product was filtered off and crystallized from acetonitrile. The product was filtered off and dried, yielding 0.120 parts (55%) of 7-azido-3-[2-[4-(4-fluorobenzoyl)-1-piperidinyl]ethyl]-2,4(1H,3H)quinazolinedione; mp. 193.7° C. (28).

In a similar manner there was also prepared:
6-azido-3-[2-[4-(4-fluorobenzoyl)-1-piperidinyl]ethyl]-2,4(1H,3H)-quinazolinedione; mp. 245.8° C. (29).

EXAMPLE 24

To a stirred solution of 0.205 parts of 7-amino-3-[2-[4-(4-fluorobenzoyl)-1-piperidinyl]ethyl]-2,4(1H,3H)-quinazolinedione in 160 parts of methanol were added 150 parts of a sodium acetate solution 1M (pH=5.6). The whole was filtered and to the filtrate was added first a solution of 0.150 parts of sodium iodide in 10 parts of water and a solution of 0.282 parts of N-chloro-4-methylbenzenesulfonamide, sodium salt trihydrate in 10 parts of water. After stirring for 10 minutes at room temperature, a solution of 0.380 parts of sodium disulfurite in 10 parts of water was added. The pH of the mixture was adjusted to 9-10 with a sodium hydroxide solution 10N. The product was extracted three times with 65 parts of dichloromethane and three times with 75 parts of trichloromethane. The combined organic layers were dried, filtered and evaporated. The residue was taken up in 16 parts of acetonitrile. The whole was evaporated to dry, yielding 0.220 parts (82%) of 7-amino-3-[2-[4-(4-fluorobenzyl)-1-piperidinyl]ethyl]-8-iodo-2,4(1H,3H)-quinazolinedione; mp. 209.1° C. (30).

EXAMPLE 25

A mixture of 4.85 parts of 7-amino-3-[2-[4-(4-fluorobenzoyl)-1-piperidinyl]ethyl]-2,4(1H,3H)-quinazolinedione dihydrochloride, 4 parts of potassium acetate, 300 parts of 2-methoxyethanol, 1 part of a solution of thiophene in methanol 4% and 4 parts of poly-(oxymethylene) was hydrogenated at normal pressure and at 60° C. with 2 parts of palladium-on-charcoal catalyst 5%. After the calculated amount of hydrogen was taken up (about 8 days), the reaction mixture was diluted with 270 parts of N,N-dimethylacetamide and heated to 100° C. The catalyst was filtered off over diatomaceous earth. The filtrate was stirred and cooled and 100 parts of water were added. The precipitated product was filtered off, washed with water and stirred in 2-propanone. The product was filtered off and dried, yielding 2.3 parts (52%) of 7-(dimethylamino)-3-[2-[4-(4-fluorobenzoyl)-1-piperidinyl]ethyl]-2,4(1H,3H)-quinazolinedione; mp. 300° C. (31).

What we claim is:

1. A chemical compound having the formula

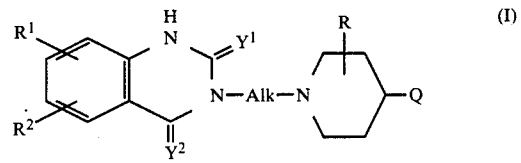
(I)

and a pharmaceutically acceptable acid addition salt thereof, wherein

R is hydrogen or $C_{1-6}$ alkyl;

$R^1$ is hydroxy, $C_{1-10}$ alkylcarbonyloxy, amino, mono- and di($C_{1-6}$alkyl)amino, $C_{1-10}$ alkyl carbonylamino, phenylmethoxy or an azido group;

$R^2$ is hydrogen or halo;

$Y^1$ and $Y^2$ are each independently O or S;

Alk is a $C_1$-$C_6$ alkanediyl radical; and

Q is 1 H-indol-3-yl or a radical of formula

—X—Ar (a)

wherein X is a bivalent radical selected from the group consisting of, >C=O; >CHOH; >CH—O—C(=O)—$R_a$; >CH$_2$; >C(O—$C_{1-6}$ alkyl)$_2$;

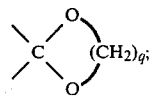

>C=NOH and >C=N—NH₂, said $R_a$ being hydrogen or $C_{1-6}$ alkyl and said q being the integer 2 or 3;

wherein Ar is phenyl optionally substituted with up to three halo-, $C_{1-6}$ alkyl-, $C_{1-6}$ alkyloxy-, trifluoromethyl or amino groups, thienyl or pyridinyl.

2. A chemical compound according to claim 1 wherein $R^1$ is hydrogen, amino, acetylamino or azido, $R^2$ and R are both hydrogen and Q is —CO—Ar.

3. A chemical compound according to claim 2 wherein Ar is halophenyl.

4. A chemical compound according to claim 1 wherein the compound is 3-[2-[4-(4-fluorobenzoyl)-1-piperidinyl]ethyl]-6-hydroxy-2,4(1H,3H)-quinazolinedione.

5. A chemical compound according to claim 1 wherein the compound is 7-amino-3-[4-(4-fluorophenyl)-1-piperidinyl]butyl-2,4(1H,3H)-quinazolinedione.

6. A chemical compound according to claim 1 wherein the compound is 7-azido-3-[2-[4-(4-fluorobenzoyl)-1-piperidinyl]ethyl]-2,4-(1,3H)-quinazolinedione.

7. A serotonin-antagonistic composition comprising an inert carrier and as an active ingredient an effective serotonin-antagonistic amount of a chemical compound having the formula

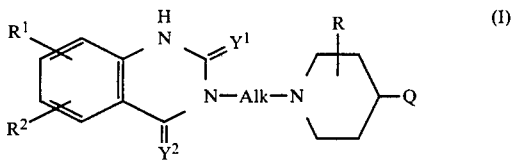

or a pharmaceutically acceptable acid addition salt thereof, wherein

R is hydrogen or $C_{1-6}$ alkyl;

$R^1$ is hydroxy, $C_{1-10}$ alkylcarbonyloxy, amino, mono- and di-($C_{1-6}$alkyl)amino, $C_{1-10}$ alkylcarbonylamino, phenylmethoxy or an azido group;

$R^2$ is hydrogen or halo;

$Y^1$ and $Y^2$ are each independently O or S;

Alk is a $C_1$-$C_6$ alkanediyl radical; and

Q is 1 H-indol-3-yl or a radical of formula

—X—Ar (a)

wherein X is a bivalent radical selected from the group consisting of, >C=O; >CHOH; >CH—O—C(=O)—$R_a$; >CH₂; >C(O—$C_{1-6}$ alkyl)₂;

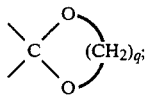

>C=NOH and >C=N—NH₂, said $R_a$ being hydrogen or $C_{1-6}$ alkyl and said q being the integer 2 or 3;

wherein Ar is phenyl optionally substituted with up to three halo-, $C_{1-6}$ alkyl-, $C_{1-6}$ alkyloxy-, trifluoromethyl or amino groups, thienyl or pyridinyl.

8. A serotonin-antagonistic composition according to claim 7 wherein $R^1$ is hydroxy, amino, acetylamino, or azido, $R^2$ and R are both hydrogen and Q is —CO—Ar.

9. A serotonin-antagonistic composition according to claim 8 wherein Ar is halophenyl.

10. A serotonin-antagonistic composition according to claim 7 wherein the compound is 3-[2-[4-(4-fluorobenzoyl)-1-piperidinyl]-ethyl]-6-hydroxy-2,4(1H,3H)-quinazolinedione.

11. A serotonin-antagonistic composition according to claim 7 wherein the compound is 7-amino-3-[4-(4-fluorobenzoyl)-1-piperidinyl]butyl-2,4(1H,3H)-quinazolinedione.

12. A serotonin-antagonistic composition according to claim 7 wherein the compound is 7-azido-3-[2-[4-(4-fluorobenzoyl)-1-piperidinyl]ethyl]-2,4-(1,3H)-quinazolinedione.

13. A method of treating warm-blooded animals suffering from diseases according to the vascular bed in which excessive serotonin release occurs which comprises the administration thereto of an effective serotonin-antagonistic amount of a chemical compound having the formula

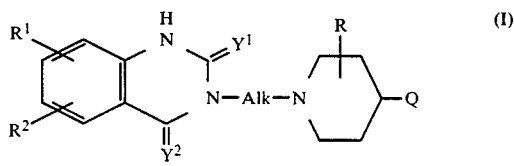

or a pharmaceutically acceptable acid addition salt thereof, wherein

R is hydrogen or $C_{1-6}$ alkyl;

$R^1$ is hydroxy, $C_{1-10}$ alkylcarbonyloxy, amino, mono- and di-($C_{1-6}$alkyl)amino, $C_{1-10}$ alkylcarbonylamino, phenylmethoxy or an azido group;

$R^2$ is hydrogen or halo;

$Y^1$ and $Y^2$ are each independently O or S;

Alk is a $C_1$-$C_6$ alkanediyl radical; and

Q is 1 H-indol-3-yl or a radical of formula

—X—Ar (a)

wherein X is a bivalent radical selected from the group consisting of, >C=O; >CHOH; >CH—O—C(=O)—$R_a$; >CH₂; >C(O—$C_{1-6}$ alkyl)₂;

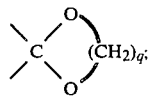

>C=NOH and >C=N—NH₂, said $R_a$ being hydrogen or $C_{1-6}$ alkyl and said q being the integer 2 or 3;

wherein Ar is phenyl optionally substituted with up to three halo-, $C_{1-6}$ alkyl-, $C_{1-6}$ alkyloxy-, trifluoromethyl or amino groups, thienyl or pyridinyl.

14. A method according to claim 13 wherein $R^1$ is hydroxy, amino, acetylamino or azido, $R^2$ and R are both hydrogen and Q is —CO—Ar.

15. A method according to claim 14 wherein Ar is halophenyl.

16. A method of treating warm-blooded animals according to claim 13 wherein the compound is 3-[2-[4-(4-fluorobenzoyl)-1-piperidinyl]ethyl]-6-hydroxy-2,4(1H,3H)-quinazolinedione.

17. A method of treating warm-blooded animals according to claim 13 wherein the compound is 7-amino-3-[4-(4-fluorobenzoyl)-1-piperidinyl]butyl-2,4(1H3,H)-quinazolinedione.

18. A method of treating warm-blooded animals according to claim 13 wherein the compound is 7-azido-3-[2-[4-(4-fluorobenzoyl)-1-piperidinyl]ethyl]-2,4-(1,3H)-quinazolinedione.

* * * * *

UNITED STATES PATENT AND TRADEMARK OFFICE
CERTIFICATE OF CORRECTION

PATENT NO. : 4,665,075
DATED : May 12, 1987
INVENTOR(S) : Vandenberk, et al.

It is certified that error appears in the above-identified patent and that said Letters Patent is hereby corrected as shown below:

Claim 5, line 17, "phenyl)" should be -- benzoyl) --.

Signed and Sealed this

Twenty-seventh Day of October, 1987

*Attest:*

DONALD J. QUIGG

*Attesting Officer*   *Commissioner of Patents and Trademarks*